US009420997B2

(12) United States Patent
Wong

(10) Patent No.: US 9,420,997 B2
(45) Date of Patent: Aug. 23, 2016

(54) MOTION ARTIFACT SUPPRESSION IN ULTRASOUND DIAGNOSTIC IMAGING

(75) Inventor: King Yuen Wong, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 785 days.

(21) Appl. No.: 13/523,725

(22) Filed: Jun. 14, 2012

(65) Prior Publication Data

US 2013/0336560 A1 Dec. 19, 2013

(51) Int. Cl.

| | |
|---|---|
| ***G06K 9/00*** | (2006.01) |
| ***A61B 8/08*** | (2006.01) |
| ***A61B 8/06*** | (2006.01) |
| ***G01S 15/89*** | (2006.01) |

(52) U.S. Cl.

CPC ................ *A61B 8/5207* (2013.01); *A61B 8/06* (2013.01); *A61B 8/488* (2013.01); *A61B 8/5223* (2013.01); *A61B 8/5276* (2013.01); *G01S 15/8981* (2013.01)

(58) Field of Classification Search

None

See application file for complete search history.

(56) References Cited

U.S. PATENT DOCUMENTS

| | | | | |
|---|---|---|---|---|
| 3,710,792 | A * | 1/1973 | Light | 600/457 |
| 5,349,525 | A | 9/1994 | Dunki-Jacobs et al. | |
| 5,445,156 | A | 8/1995 | Daft et al. | |
| 5,487,389 | A | 1/1996 | Banjanin et al. | |
| 5,494,037 | A | 2/1996 | Banjanin et al. | |
| 5,544,659 | A | 8/1996 | Banjanin | |
| 5,623,929 | A | 4/1997 | Weng | |
| 5,664,575 | A | 9/1997 | Banjanin et al. | |
| 5,860,930 | A | 1/1999 | Guracar | |
| 6,309,357 | B1 | 10/2001 | Guracar et al. | |
| 6,544,184 | B1 | 4/2003 | Guracar | |
| 6,689,064 | B2 | 2/2004 | Hager et al. | |
| 2005/0075569 | A1 | 4/2005 | Li et al. | |
| 2005/0131300 | A1 * | 6/2005 | Bakircioglu et al. | 600/453 |
| 2006/0036175 | A1 | 2/2006 | Guracar et al. | |
| 2006/0079778 | A1 * | 4/2006 | Mo et al. | 600/447 |
| 2007/0204671 | A1 * | 9/2007 | Sliwa et al. | 73/1.83 |
| 2007/0291591 | A1 * | 12/2007 | Peng | G01S 15/104 367/101 |
| 2009/0024034 | A1 | 1/2009 | Moreau-Gobard et al. | |
| 2009/0221916 | A1 | 9/2009 | Konofagou et al. | |
| 2011/0137156 | A1 * | 6/2011 | Razzaque et al. | 600/424 |
| 2012/0136248 | A1 * | 5/2012 | Kanayama et al. | 600/437 |

* cited by examiner

*Primary Examiner* — Andrew Moyer

(57) ABSTRACT

Motion artifacts are suppressed for motion imaging in medical diagnostic ultrasound. Spatial correlation is used to detect motion, including any lateral motion. Some aspect of clutter filtering may be set based on the amount of spatial correlation or detected motion. The shift for frequency mixing, wall filter cutoff frequency, and/or velocity threshold may be set.

20 Claims, 5 Drawing Sheets

30 Acquire Frames of Data
32 Detect Motion
34 Set Clutter Filter based on Detected Motion
36 Set Velocity Threshold
38 Set Clutter Shift
40 Set Cutoff Frequency
42 Clutter Filter
44 Estimate Flow
46 Generate Image

MOTION ARTIFACT SUPPRESSION IN ULTRASOUND DIAGNOSTIC IMAGING

BACKGROUND

This present embodiments relate to medical diagnostic ultrasound. In particular, suppression of motion artifacts is provided for medical diagnostic ultrasound.

When imaging flow, the sonographer may move a transducer relative to a patient in an effort to identify a region of interest. When color, flow imaging is active, the motion may be detected as flow, causing a flash or motion artifact.

Motion artifacts may be suppressed. The shift in the clutter spectrum due to motion is determined. The clutter spectrum is frequency mixed with an equal but opposite shift. The mixing brings the clutter peak to DC. A wall filter removes information at DC. The wall filter cutoff may also change as a function of the amount of shift.

Motion does not necessarily cause a shift in clutter spectrum. Only the axial component of the motion produces a shift in the clutter spectrum. The lateral component produces little or no shift. Shifting the distorted spectrum to DC may not be effective in situations with lateral motion.

Axial motion also distorts the symmetry of the clutter spectrum. The degree of distortion depends on the amount of motion. Without motion, the clutter spectrum is normally mostly symmetric. Shifting the distorted spectrum to DC is not only non-effective, but sometimes detrimental because of the false detection after wall filtering.

BRIEF SUMMARY

By way of introduction, the preferred embodiments described below include a method, system, computer readable medium, and instructions for motion artifact suppression in medical diagnostic ultrasound. Spatial correlation is used to detect motion, including any lateral motion. Some aspect of clutter filtering may be set based on the amount of spatial correlation or detected motion. The shift for frequency mixing, wall filter cutoff frequency, and/or velocity threshold may be set.

In a first aspect, a method is provided for motion artifact suppression in medical diagnostic ultrasound. First and second frames of ultrasound data representing flow power response from a patient are acquired. The first and second frames of ultrasound data are spatially correlated, resulting in a correlation coefficient. A first characteristic of a clutter filter is set as a function of the correlation coefficient. The clutter filter is set with the first characteristic clutter filters. An image of the patient is generated from an output of the clutter filtering.

In a second aspect, a non-transitory computer readable storage medium has stored therein data representing instructions executable by a programmed processor for motion artifact suppression in medical diagnostic ultrasound. The storage medium includes instructions for detecting at least lateral motion between data acquired at different times, determining a threshold value for velocity as a function of the detected at least lateral motion, estimating velocities, and thresholding the velocities with the threshold value for velocity.

In a third aspect, a system is provided for motion artifact suppression in medical diagnostic ultrasound. A beamformer is operable to acquire data. A mixer is operable to shift a frequency of the data. A wall filter is operable to high pass filter an output of the mixer. An estimator is operable to estimate flow from an output of the wall filter. A thresholder is operable to threshold the estimated flow. A processor is configured to estimate a degree of motion from two- or three-dimensional spatial correlation and to adapt a setting of the mixer, the wall filter, the thresholder, or combinations thereof based on the degree of motion.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The degree of motion between successive color flow frames is estimated. Frame correlation based on clutter data itself may be more reliable than based on B-mode data. Frame correlation is used to estimate motion due to both axial and lateral movement. A non-computational intensive autocorrelation coefficient is used. Alternatively, a motion vector is used.

The resulting motion estimate is responsive to any lateral and any axial motion, so is used to adjust one or more clutter rejection parameters to better suppress motion artifacts Doppler estimates of clutter shift may become less reliable with large and complex motion. The motion filter cutoff, shifting frequency, and/or post-detection velocity threshold are adjusted to suppress motion artifacts from areas and/or frames of high motion while maintaining low flow sensitivity to areas and/or frames of relatively less motion.

A combination of Doppler estimates for axial clutter shift and spatial correlation may be used. Doppler techniques for detecting axial motion shifts from the clutter spectrum and shifting the clutter spectrum may be used for smaller motion. Frame correlation and corresponding adjustments may be used for larger motion.

Although setting clutter rejection based on spatial correlation may lead to lower low flow sensitivity when there is large motion because of increased rejection, the suppression of motion artifacts may outweigh the loss in low flow sensitivity. When motion ceases, the rejection falls back to a normal level and low flow sensitivity recovers.

Figure 1:
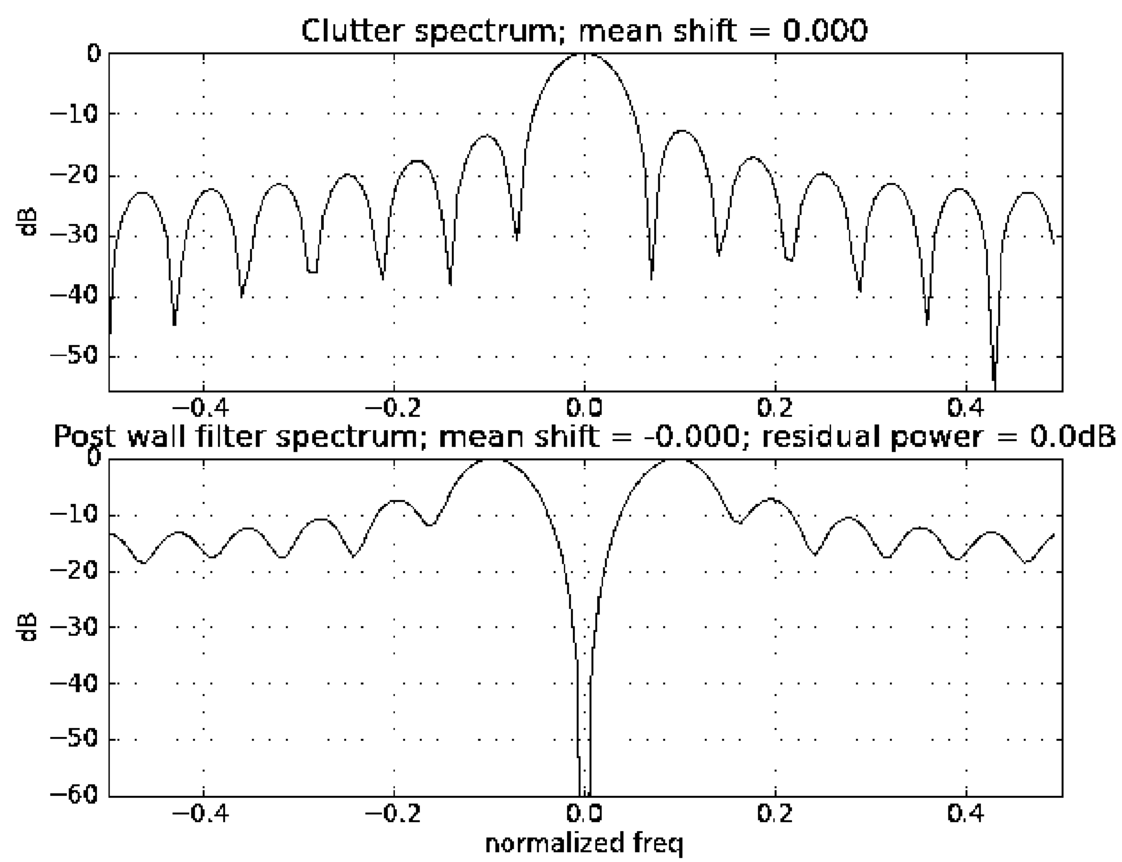
FIG. 1 illustrates a clutter spectrum and post wall filter spectrum according to one example with no motion.

FIGS. 1-4 show a clutter spectrum (top) and a spectrum after wall filtering (bottom) in various situations. FIG. 1 shows the simulated clutter spectrum of a stationary pin target. The lower plot shows the spectrum after application of a wall filter. The clutter spectrum is generally symmetric about DC, resulting in a mean shift, if any, close to zero. Although the pin target has high residual clutter energy as seen by the incomplete clutter rejection in the lower plot, the resulting pin may be suppressed by a post detection velocity threshold. The velocity threshold may be set low for low flow sensitivity. For comparison purposes of later plots of FIGS. 2-4, this residual energy is considered to be O dB.

Figure 2:
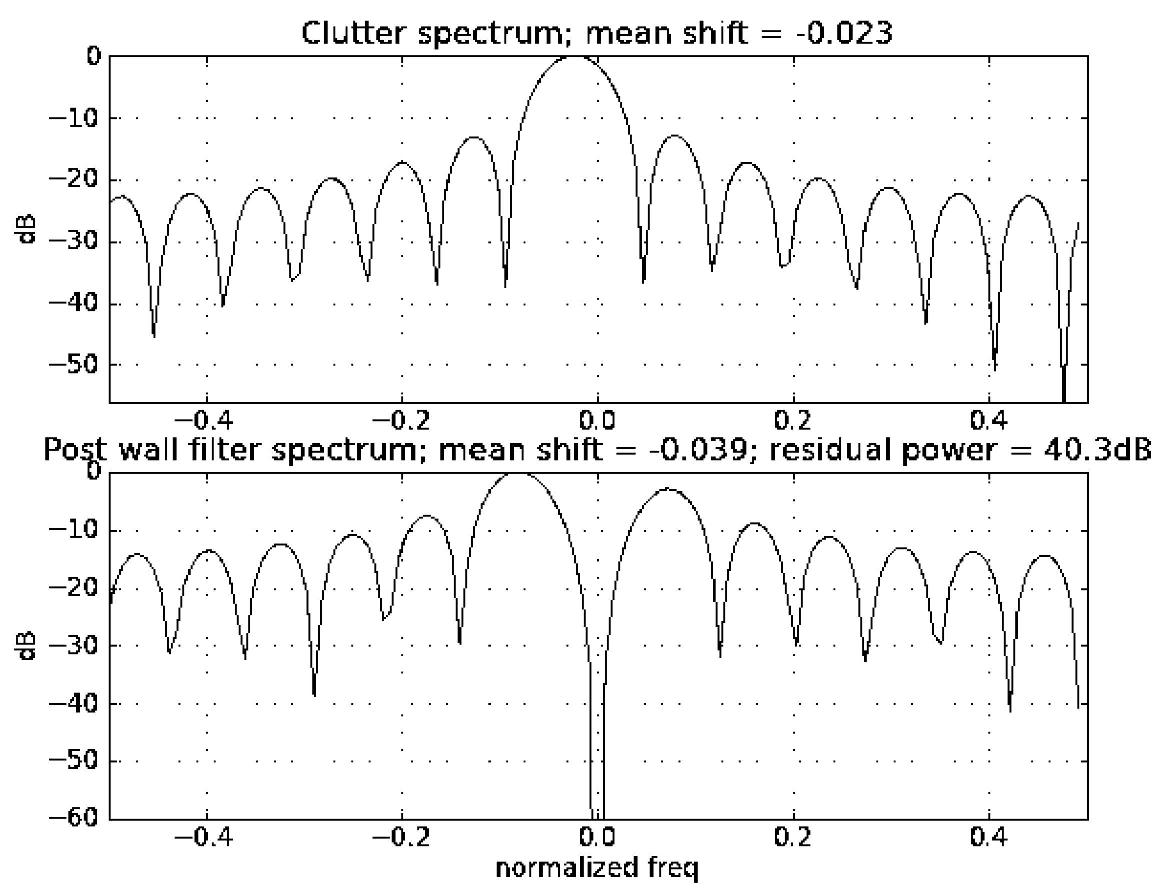
FIG. 2 illustrates a clutter spectrum and post wall filter spectrum according to one example with axial motion.

The upper plot of FIG. 2 shows the clutter spectrum of the same time as FIG. 1, but with motion mostly axially with respect to the transducer. This causes the clutter spectrum to shift and produces a net mean negative flow after application of the wall filter as shown by the spectral peak at about −0.09 normalized frequency.

Figure 3:
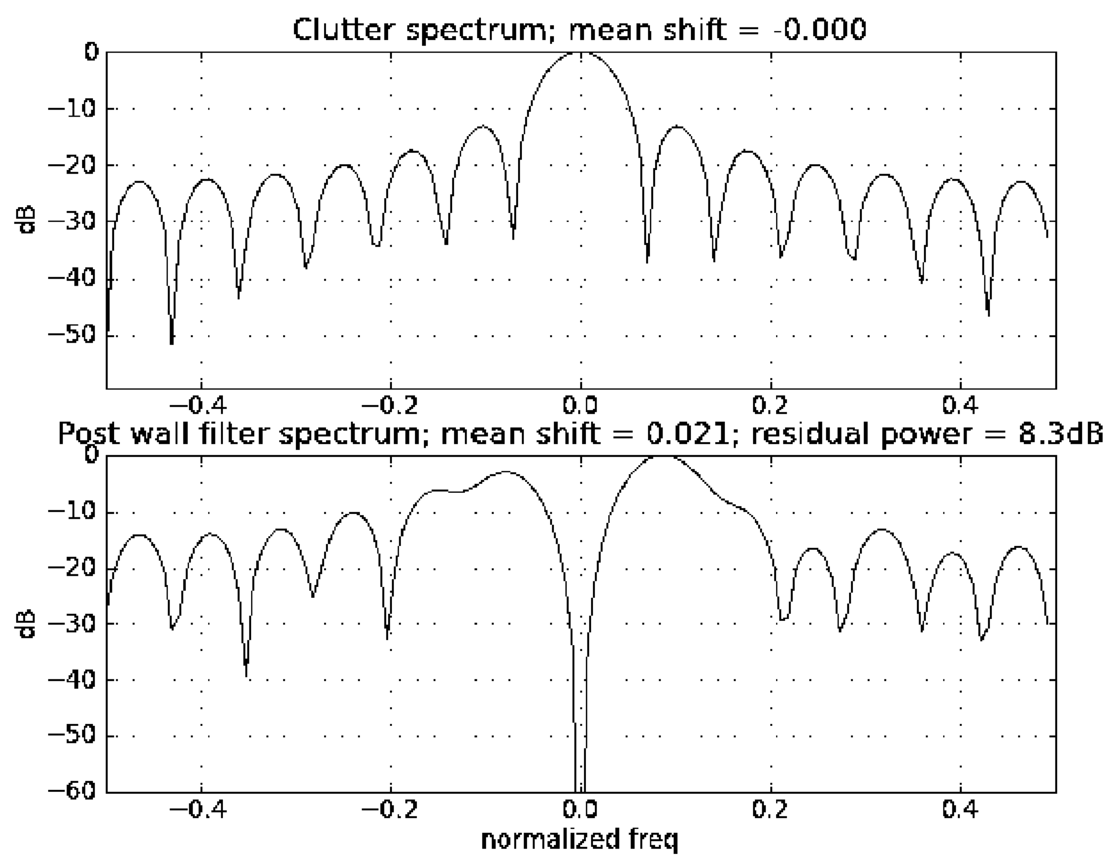
FIG. 3 illustrates a clutter spectrum and post wall filter spectrum according to one example with lateral motion.

To address this axial motion, the clutter spectrum may be shifted back to DC before application of the wall filter. FIG. 3 shows a problem with shifts due to lateral motion rather than axial motion. The upper plot shows the clutter spectrum where the pin moves mostly laterally with respect to the transducer. The clutter spectrum shows little shift even though the pin is moved. The lower plot shows the spectrum after application of the wall filter. Instead of introducing a shift in the spectrum, the lateral motion distorts the symmetry of the spectrum. The distortion is enough to cause a net mean positive, but false flow indication. This net shift is a function of the symmetry distortion and may be high relative to actual blood flow. The residual power is also higher because the clutter spectrum has spread. As a result, the false flow may pass the post-detection power threshold and energy threshold, manifested as artifacts on the image. Calculating the spectral variance of the clutter to address the artifacts may not be sufficient, as even undetectable changes in variance may be enough to cause spectral distortion and spreading that contributes significantly to motion artifacts.

Figure 4:
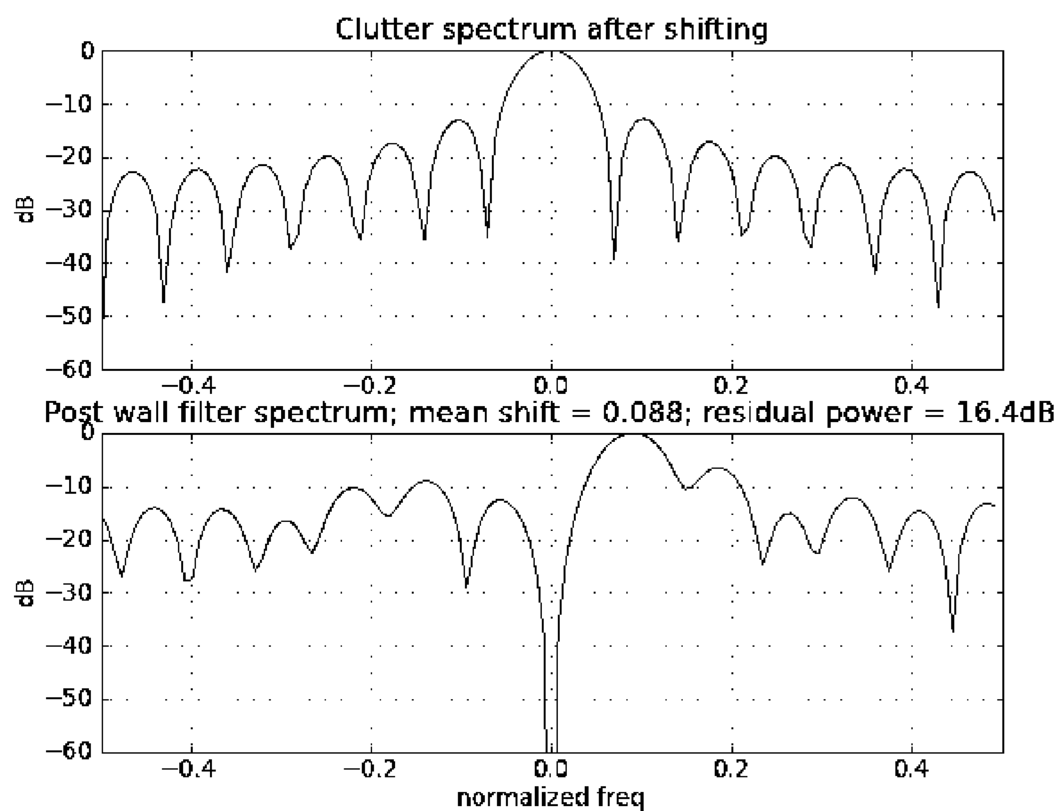
FIG. 4 illustrates a clutter spectrum and post wall filter spectrum according to one example with the clutter spectrum shifted to counteract motion.

FIG. 4 shows shifting the clutter spectrum due to axial motion back to DC in the upper plot. The resultant residual power is significantly reduced from 40.3 dB (FIG. 2) to 16.4 dB. The residual power is not low enough to be rejected by the post detection power threshold. There is also a net mean positive shift, due to the spectral symmetry distortion caused by the motion. The positive shift may be large enough to be considered valid flow by the post detection velocity threshold. Artifacts result.

In general, when motion is small, the symmetry distortion is negligible and clutter shifting may be beneficial although the improvement may not be significant. When motion is large, symmetry distortion becomes significant and more aggressive techniques, such as setting based on spatial correlation or detected motion, may effectively suppress motion artifacts. The degree of symmetry distortion and spreading also increases as motion is increased. As result, the mean Doppler shift becomes less indicative of the spectral peak. Using spatial correlation or motion detection may counteract symmetry distortion and/or spreading. Frame correlation is used estimate motion instead of or in addition to detecting Doppler shift from clutter. Both axial and lateral motion between frames may be detected and dealt with by clutter filtering.

Clutter filtering includes actions to reduce clutter. The actions include wall filtering. Other actions included as clutter filtering may be preparation of the signals for wall filtering, such as applying a mean shift. Other actions included as clutter filtering may be post-wall filtering processing, such as application of velocity or energy thresholds to estimates detected from wall filtered data.

Figure 5:
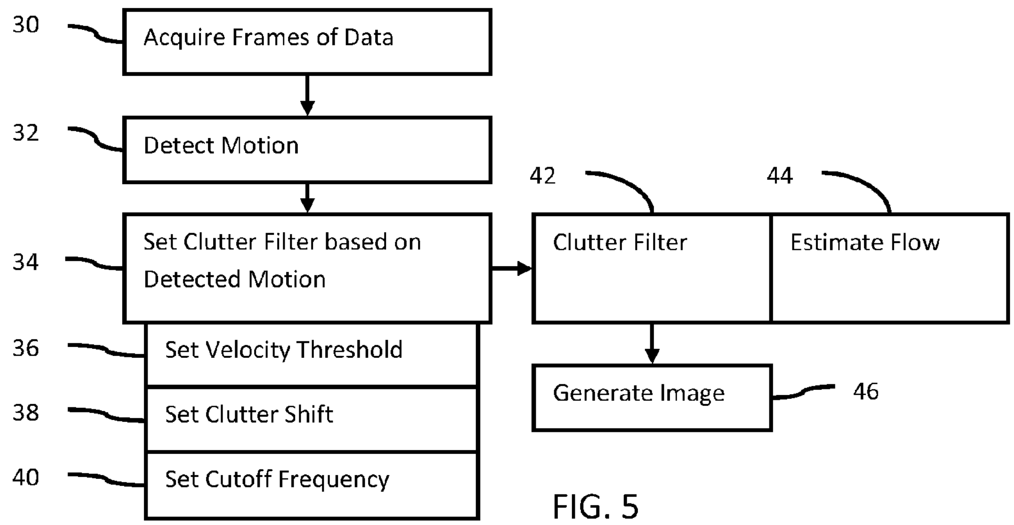
FIG. 5 is a flow chart of one embodiment of a method for motion artifact suppression in medical diagnostic ultrasound.

FIG. 5 shows a method for color flow motion artifact suppression in medical diagnostic ultrasound. The method is performed by the system 10 of FIG. 6 or a different system. The acts of FIG. 5 are performed in the order shown or a different order. Additional, different, or fewer acts than shown in FIG. 5 may be used. For example, one, two, all three, or none of acts 36, 38, and 40 are performed. As another example, act 46 is not provided. The acts of FIG. 5, described below, may be implemented in different ways. At least one example embodiment is provided below, but other embodiments are possible.

In act 30, frames of ultrasound data from different times are acquired. The data is acquired by scanning or from memory. Data acquired from memory is previously acquired by scanning. The data is received while scanning or by transfer. In one embodiment, the data is acquired during real-time scanning (i.e., data acquired and processed in a same imaging session) or as the scanning occurs.

The ultrasound data represents a plane or volume of a patient. A volume is scanned along different planes or other distribution of scan lines within the volume. The scanned volume or plane is an interior of an object, such as the patient. The data representing the patient is formed from spatial sampling of the object. The spatial samples are for locations distributed in an acoustic sampling grid. A frame is data representing the scanned region (plane or volume) at a time. The frame of data represents an entire scanned region or region of interest.

Spatial samples along one or more scan lines are received. Where the transmit beam insonifies just one receive scan line, the samples along that scan line are received. Where the transmit beam insonifies multiples scan lines, then samples along the multiple scan lines are received. For example, receive beamforming is performed along at least thirty distinct receive lines in response to one broad transmit beam. To generate the samples for different receive beams, parallel receive beamformation is performed so that the different receive beams are sampled at a same time. Spatial samples are acquired for a plurality of receive lines in response to one and/or in response to sequential transmit beams. Alternatively, Fourier or other processing may be used to form the spatial samples.

The scanning may be performed a plurality of times. The acts are repeated to scan sequentially different portions of the field of view. Alternatively, performing once acquires the data for the entire field of view.

The complete volume or plane is scanned at different times. Scanning at different times acquires spatial samples associated with flow. Any now known or later developed pulse sequences may be used. A sequence of at least two (flow sample count or ensemble) transmissions is provided along each scan line. Any pulse repetition frequency, flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a frame of data representing the patient at a given time are acquired using transmissions from different times. The estimates from different scan lines may be acquired sequentially, but rapidly enough to represent a same time from a user perspective.

Multiple scans are performed to acquire estimates for different times. By including beamformed samples from different ensembles, estimates associated with different times are acquired. The ensembles for different times may include one or more of the same samples, such as using a moving window in generating estimates. Alternatively, the ensembles do not share samples.

The frames of ultrasound data represent flow power response from a patient. Flow power may be clutter power. Flow data is generated from the spatial or beamformed samples of the ensemble. Any flow data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. Color is used to distinguish from spectral Doppler imaging, where the power spectrum for a range gate is estimated. The change in frequency between two samples for the same location at different times indicates the velocity. A sequence of more than two samples may be used to estimate the color Doppler parameter values.

Multiple frames of flow data are acquired to represent the volume or plane at different times. Data from samples acquired at different times is used for estimating the flow data for different frames. In the sequence of frames, some frames are acquired prior to other frames and other frames are acquired after previous frames. The group of frames used for correlation may be consecutive or separated by other frames in the sequence.

Flow power may be obtained for correlation or motion detection. In one embodiment, the clutter strength is estimated. The Doppler power is estimated from the ensemble. Energy or magnitude may be estimated as the power. To estimate clutter strength, the samples of the ensemble are not clutter filtered and/or are not wall filtered. Some filtering may be provided, but the filtering allows a majority or most of the clutter information to pass for use in estimation.

The clutter strength may be estimated from all or a sub-set of samples of a given ensemble. For example, the unfiltered clutter power is determined from an averaged or summed power of all of the samples of the ensemble. As another example, the unfiltered clutter power is determined from the power or magnitude of just a single member of the color ensemble. Any member may be used, such as a first or middle member. Any sub-set may be used, such as averaging half of the samples of an ensemble.

In one embodiment, a measure of the clutter strength $M_{p,q}$ (f) is calculated for the each sample in range, denoted by p, and azimuth, denoted by q. The sample may be in an in-phase and quadrature (I/Q), radio frequency, or other format. The measure for clutter strength is made for every frame f, such as for two or more frames, from the samples of the ensemble, e. The measure may be represented as:

$$m_{p,q}(f)=\Sigma I^2_{p,q}(e,f)+Q^2_{p,q}(e,f)$$ using an ensemble average or $$m_{p,q}(f)=I^2_{p,q}(0,f)+Q^2_{p,q}(0,f)$$ using a single ensemble member;

where the clutter strength or flow power of the clutter is represented by either of $M_{p,q}(f)=m_{p,q}(f)$ to use power or the sqrt of $m_{p,q}(f)$ to use magnitude.

Other estimates of clutter strength or flow power may be used. Additional data may be acquired, such as velocity or variance data.

In act 32, lateral motion is detected. Lateral is along the azimuth or elevation direction as opposed to axial or depth direction. Azimuth, elevation, and axial are relative to the transducer, where axial is along a beam orthogonal to a center of the transducer, azimuth is a perpendicular to axial and along a distribution of the elements for a one dimensional array, and elevation is perpendicular to the other two dimensions.

Motion in other directions may be detected as well. One measure may detect motion in multiple directions. For example, an amount of correlation may detect motion along any direction or combinations of directions. A scalar value indicates motion regardless of the direction. This scalar represents detection of lateral and axial motion. In another example, a one, two or three-dimensional motion vector (i.e., magnitude and direction) is detected. Separate measures may be made to detect motion in separate directions.

The motion is detected between data acquired at different times. The data representing the power of flow or clutter strength from different times is used. The motion is detected from the frames or sub-sets of data from frames of different times.

While B-mode data may be used to detection motion, using data representing the flow power or clutter strength may more likely reflect motion resulting in artifacts in flow imaging. Since the flow is of interest, flow data is more likely available for the locations of interest. B-mode data may be unavailable in flow regions.

Motion is detected by spatially correlating the data from the different times. One frame of data is correlated with another frame of data. Three or more frames may be correlated in other embodiments. The spatial correlation indicates a similarity in one, two, or three dimensions. Data spaced along the dimensions are compared.

In one embodiment, spatially correlating the data provides a correlation coefficient. The correlation coefficient is a measure of the motion, including any lateral motion, between the frames. A scalar value representing an amount of similarity is calculated. The correlation coefficient is calculated without spatial registration of the frames other than being for scans of a same or similar region. An offset of one frame relative to another frame is not used for calculating the correlation coefficient. Frame correlation may simply be calculating the autocorrelation coefficient between frames. Alternatively, the frames are translated and/or rotated relative to each other and correlation calculated for different relative positions to identify a maximum correlation coefficient.

All of the Doppler, flow, power, or clutter strength data for one frame is correlated with all of the data for another frame. Sub-sets of data may be correlated. Frame correlation may include calculating local motion vectors between frames. Two or more motion vectors are calculated between any two frames. The clutter filtering may be the same for entire frames or may adapt locally by location or sub-regions. If motion vectors are used, the adjustments to clutter shifting, wall filter cutoff and post detection velocity threshold may be changed from sample to sample or between regions.

In one embodiment, the frame correlation coefficient is calculated as:

$$C(f)=(\Sigma_{p,q}M_{p,q}(f)*M_{p,q}(f-1))/(\text{sqrt of}(|\Sigma_{p,q}M^2_{p,q}(f)||\Sigma_{p,q}M^2_{p,q}(f)|)).$$

This correlation coefficient, C, is a frame motion estimate. Other measures of similarity may be used to detect the motion or determine correlation. For example, a sum of absolute differences is calculated. A minimum sum of absolute differences may be used where a maximum correlation or local motion vectors are used. Cross-correlation or other measure of similarity may be used.

In act 34, one or more characteristics of clutter filtering are set. The characteristics are set as a function of the correlation coefficient. The amount of motion detected is used for setting. Any mapping function may be used, such as linear or non-linear relationship of the correlation coefficient to settings. Alternatively, that sufficient motion is detected is used for setting. The settings are binary—one setting for little or no motion and another setting for more motion.

Different clutter filtering techniques may be used based on the correlation coefficient. In addition or an alternative to setting a characteristic of clutter filtering, different approaches may be selected. For example, when little or no motion is detected from frame correlation, the clutter spectrum is shifted to counteract any detected shift. When large motion is detected from frame correlation, the shifting of clutter spectrum is reduced or disabled, but another approach is implemented. The other approach may be increasing the wall filter cutoff and/or post detection velocity threshold. The increase may be a function of the degree of motion.

The characteristic is set by selecting a value. For example, an experimentally determined mapping function provides a velocity threshold, wall filter cutoff, or clutter spectrum shift based on an input amount of motion (e.g., an input correlation coefficient). The setting is an original or independently determined value.

In other embodiments, the setting is an adjustment to a value. For example, characteristics may be established based on previous use, user settings, or operation pursuant to a particular imaging application. The setting as a function of the detected motion changes the value, such as increasing or decreasing the value. The amount of change may be mapped to the amount of motion. The adjustments to the shifting, $\Delta S_{p,q}(f)$, wall filter cutoff, $\Delta W_{p,q}(f)$ and post detection velocity threshold, $\Delta V_{p,q}(f)$ are calculated based on either the auto-correlation coefficient, local motion vectors, or local correlation measures.

The settings are applied for entire frames or locally. For entire frames, the same settings are used for the different values representing different spatial locations within the frame. The clutter filtering is the same for an entire frame. For local application, the settings may be different for different locations. The clutter filtering adapts for different locations or groups of locations in a same frame.

Any frequency of setting may be used, such as performing the detection and setting periodically. Every number of seconds, minutes, or frames may trigger adjustment. Alternatively, the detection is on-going at any frequency and a change in motion triggers setting. Other triggers may be used without ongoing detection.

The motion, including any motion due to lateral shift, is used to set the clutter filtering for subsequent data. Alternatively, the data used to estimate the flow power or clutter strength is processed again with the new settings of the clutter filter.

Any characteristic of clutter filtering may be set. The wall filter cutoff frequency, type of wall filter, spectrum shift, velocity threshold, power threshold, and/or other characteristic is set. In one embodiment represented by act 38, a shift applied to a clutter spectrum prior to filtering is set based on the detected lateral motion. For setting for entire frames, the shift is represented as:

$$\Delta S_{p,q}(f)=S_F(C(f)).$$

For setting the shift differently for different locations within a frame, the shift is represented as:

$$\Delta S_{p,q}(f)=S_F(C_{p,q}(f)).$$

The adjustment or adjustments are applied in addition to any other shifting. The adjustment may shift more for greater motion. In some embodiments, the motion may be very large, so shifting is not used. Any thresholds or range for when to use shifting or when not to may be used. The adjustment is represented as:

$$S_{p,q,final}(f)=S_{p,q}+\Delta S_{p,q}(f),$$

where $S_{p,q}$ denotes the sample dependent clutter shifting had the adjustment for setting not been used.

In another embodiment represented by act 40, the cutoff frequency of the clutter filtering is set based on the detected lateral motion. For setting for entire frames, the cutoff frequency is represented as:

$$\Delta W_{p,q}(f)=W_F(C(f)).$$

For setting the cutoff frequency differently for different locations within a frame, the cutoff frequency is represented as:

$$\Delta W_{p,q}(f)=W_F(C_{p,q}(f)).$$

The adjustment or adjustments are applied in addition to any other wall filtering cutoff frequency. The adjustment may increase the cutoff frequency for greater motion. The adjustment is represented as:

$$W_{p,q,final}(f)=W_{p,q}+\Delta W_{p,q}(f),$$

where $W_{p,q}$ denotes the sample dependent cutoff frequency had the adjustment for setting not been used.

In another embodiment represented by act 36, the velocity threshold of the clutter filtering is set based on the detected lateral motion. The threshold for setting low velocity to a noise or zero level is determined.

For setting for entire frames, the velocity threshold is represented as:

$$\Delta V_{p,q}(f)=V_F(C(f)).$$

For setting the velocity threshold differently for different locations within a frame, the velocity threshold is represented as:

$$\Delta V_{p,q}(f)=V_F(C_{p,q}(f),$$

The adjustment or adjustments are applied in addition to any other post detection rejection. The adjustments provide a higher threshold for greater motion. The adjustment is represented as:

$$V_{p,q,final}(f)=V_{p,q}+\Delta V_{p,q}(f),$$

where $V_{p,q}$ denotes the sample dependent cutoff frequency had the adjustment for setting not been used.

In act 44, flow is estimated. Using the ensembles acquired for setting the clutter filtering or other ensembles, the velocity, energy (power), and/or variance are estimated. The estimates are performed for a plurality of locations, such as each location in a flow or moving tissue region of interest. Doppler, correlation, or other processing is used to estimate the flow.

In act 42, clutter filtering is performed. The clutter filtering is performed with the setting or settings determined in act 34. Other considerations or variables may be used for any final settings of the various characteristics of the clutter filtering.

The clutter filtering is performed before, during, and/or after the estimation of flow in act 44. For example, the spectrum shift is applied to the ensemble prior to estimation. The ensemble of samples for a given location is mixed with a signal at a desired frequency to shift the spectrum associated with the samples. Other shifting may be used.

As another example, the wall filtering to remove slow moving tissue or low flow information is performed on the data of the ensemble prior to estimation. The wall filtering is of signals in the pulse sequence (flow sample count) for estimating motion at a given time. A given signal may be used for estimates representing different times, such as associated with a moving window for wall filtering and estimation.

In yet another example, the velocity thresholding is applied to flow estimates (e.g., velocity and/or energy) after estimation. For a given location, the velocity is compared to the threshold. If the velocity is below the threshold, then the velocity, energy, and/or other flow estimate is set to a lower value, such as set to zero, a noise floor, or otherwise reduced. If the velocity is above the threshold, then the velocity, energy, and/or other flow estimate is maintained or not reduced. Velocity at the threshold may be treated as above or below the threshold. One or both thresholds may be adapted based on the spatial correlation. The thresholding is applied for each location in the frame or flow region.

In act 46, the clutter filtered estimates are used for imaging. An image of the flow in the patient is generated. The image is generated from an output of the clutter filtering. The clutter filtering operates on the flow estimates, such as Doppler data. The image is a color flow or tissue Doppler image. The image represents the flow, such as being a color velocity or energy image.

The flow may be overlaid or displayed with B-mode or tissue data. Two-dimensional images may be provided. A sequence of images may be provided. Three-dimensional renderings or color M-mode images may be provided.

Figure 6:
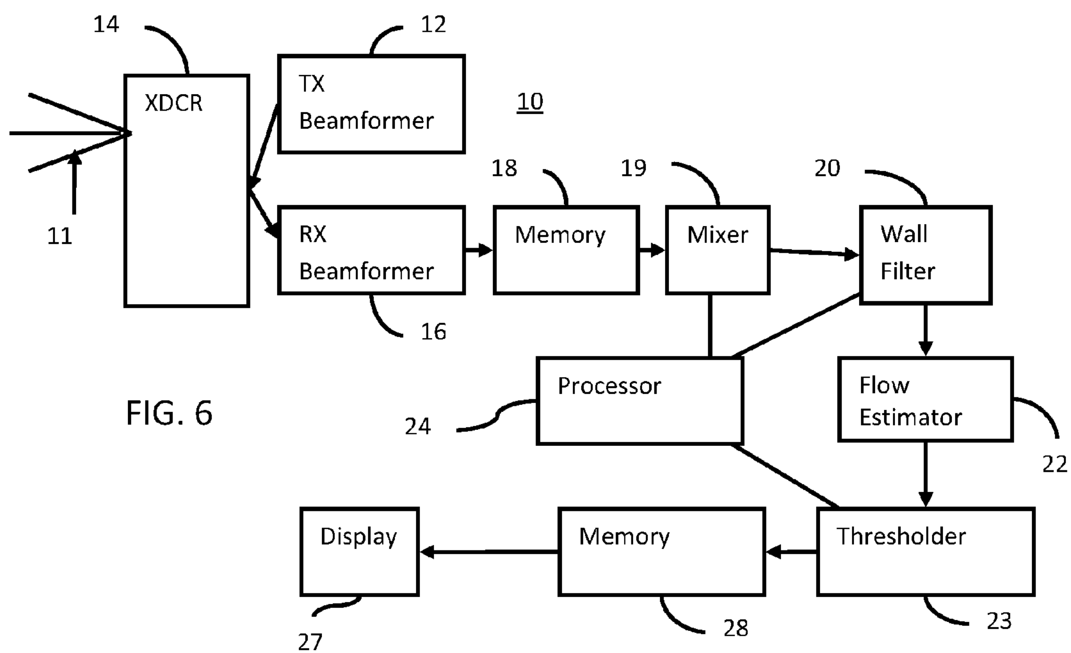
FIG. 6 is a block diagram of one embodiment of a system for motion artifact suppression in medical diagnostic ultrasound.

FIG. 6 shows a system for color flow motion artifact suppression in medical diagnostic ultrasound. The system 10 includes a transmit beamformer 12, a transducer 14, a receive beamformer 16, a memory 18, a mixer 19, a wall filter 20, a flow estimator 22, a thresholder 23, a memory 28, a processor 24, and a display 27. Additional, different or fewer components may be provided. For example, the system includes the flow estimator 22 and processor 24 without the front-end components, such as the transmit and receive beamformers 12, 16. In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5 D array, a 1.25 D array, a 1.75 D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. In one embodiment, the transmit beamformer 12 transmits beams sufficiently large to cover at least thirty distinct receive lines, and the receive beamformer 16 receives along these distinct receive lines in response to the transmit beam. The receive beamformer 16 samples the receive beams at different depths. Sampling the same location at different times obtains a sequence for flow estimation. Two or three-dimensional scanning may be provided.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more (e.g., 30, 40, or 50) receive beams in response to each transmit beam. The receive beams are collinear, parallel and offset or nonparallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such fluid velocity, multiple transmissions and corresponding receptions are performed for a substantially same spatial location. Phase changes between the different receive events indicate the velocity of the tissue or fluid. A velocity sample group corresponds to multiple transmissions for each of a plurality of scan lines 11. The number of times a substantially same spatial location, such as a scan line 11, is scanned within a velocity or flow sample group is the velocity or flow sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a three-dimensional grid.

The mixer 19 is a multiplier and programmable oscillator, digital processor, or other phase shifter. The mixer 19 shifts the mean frequency of input data. The amount of shift may be adaptive or programmable. The mixer 19 shifts a frequency of the data. The mixer 19 may be part of the filter 20 or receive beamformer 16.

The filter 20 is a wall filter, finite impulse response filter, infinite impulse response filter, analog filter, digital filter, combinations thereof, or other now known or later developed filter. In one embodiment, the filter 20 includes the mixer 19 to shift signals to baseband and a programmable high pass filter response for removing or minimizing information at frequencies at the baseband. In other embodiments, the filter 20 is a low pass, high pass or band pass filter. The filter 20 maintains higher velocity information and reduces information from slower moving tissue. In yet another embodiment, the memory 18, mixer 19, and/or the filter 20 are part of the flow estimator 22.

The filter 20 may be programmed, such as altering operation as a function of a cutoff frequency. The 6, 10 or other dB frequency may be set. The cutoff frequency establishes the bandwidth of the pass band. Other characteristics, such as the rate of drop off may be set.

The flow estimator 22 is a Doppler processor or cross-correlation processor for estimating the flow data. In alternative embodiments, another device now known or later developed for estimating velocity, energy, and/or variance from any or various input data may be provided. The flow estimator 22 receives a plurality of signals associated with a substantially same location at different times from the wall filter 20 and estimates a Doppler shift frequency, based on a change or an average change in phase between consecutive signals from the same location. Velocity is calculated from the Doppler shift frequency. Alternatively, the Doppler shift frequency is used as a velocity. The energy and variance may also be calculated.

Flow data (e.g., velocity, energy, or variance) is estimated for spatial locations in the scan volume or plane from the beamformed scan samples. For example, the flow data represents a plurality of different planes in the volume.

The thresholder 23 receives the output of the flow estimator 22 or may be included as part of the flow estimator 22. The thresholder 23 is a processor, filter, logic device, comparator, differential amplifier, or other component to apply one or more thresholds to identify sufficient motion information. For example, velocity and/or energy thresholding for identifying velocities is used.

The memory 28 is video random access memory, random access memory, removable media (e.g. diskette or compact disc), hard drive, database, or other memory device for storing B-mode and flow data. The stored data is in a polar or Cartesian coordinate format. In one embodiment, the memory 28 is a CINE memory.

The display 27 is a CRT, LCD, plasma, projector, monitor, printer, touch screen, or other now known or later developed display device. The display 27 receives RGB or other color values and outputs an image. The image may be gray scale or color image. The image represents the region of the patient scanned by the beamformer and transducer 14. The image is a color flow image based on the clutter filtered velocity, energy, and/or variance estimates.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 and/or other components of the system 10 operate pursuant to instruction provided in the memory 18, 28, or a different memory for clutter filtering in medical diagnostic ultrasound.

The processor 24 controls the mixer 19, wall filter 20, and/or thresholder 23. The processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 causes estimation of clutter data or power flow data without wall filtering. Two or more frames are estimated. A degree of motion is estimated from the frames, such as detecting a relative motion vector or a degree of correlation. The motion may include lateral motion. The correlation is based on a one, two- or three-dimensional spatial correlation.

The processor 24 adapts a setting of the mixer 19, the wall filter 20, the thresholder 23, or combinations thereof based on the degree of motion. For example, the value of the velocity threshold of the thresholder 23 is set or altered based on the degree of motion.

The instructions for implementing the processes, methods and/or techniques discussed above are provided on non-transitory computer-readable storage media or memories, such as a cache, buffer, RAM, removable media, hard drive or other computer readable storage media. In one embodiment, the instructions are for motion artifact suppression. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for motion artifact suppression in medical diagnostic ultrasound, the method comprising:

acquiring first and second frames of ultrasound data representing flow power response from a patient;

spatially correlating the first and second frames of ultrasound data, the spatially correlating providing a correlation coefficient;

setting a first characteristic of a clutter filter as a function of the correlation coefficient, the first characteristic comprising a cutoff frequency, shift, or threshold, a value for the first characteristic selected with a mapping function from a value of the correlation coefficient, where the mapping function maps greater values of the correlation coefficient to greater values for the first characteristic;

cluttering filtering with the clutter filter set with the first characteristic; and generating an image of the patient from an output of the clutter filtering.

2. The method of claim 1 wherein acquiring comprises estimating clutter strength as the flow power response.

3. The method of claim 1 wherein acquiring comprises estimating the flow power response without clutter filtering.

4. The method of claim 1 wherein acquiring comprises acquiring ensembles for flow estimation for each of the first and second frames and estimating the flow power response from averages of the ensembles or from single members of the ensembles.

5. The method of claim 1 wherein spatially correlating comprises measuring a lateral motion between the first and second frames.

6. The method of claim 1 wherein spatially correlating comprises calculating a sum of absolute differences.

7. The method of claim 1 wherein spatially correlating comprises spatially correlating the entire first frame with the entire second frame, and wherein setting comprises setting the first characteristic for filtering all locations for the image.

8. The method of claim 1 wherein spatially correlating comprises spatially correlating without an offset of the first frame relative to the second frame.

9. The method of claim 1 wherein setting the first characteristic comprises setting the shift applied to a clutter spectrum prior to filtering.

10. The method of claim 1 wherein setting the first characteristic comprises setting the cutoff frequency of the clutter filtering.

11. The method of claim 1 wherein setting the first characteristic comprises setting the threshold as a velocity threshold.

12. The method of claim 1 wherein clutter filtering comprises filtering prior to estimation of flow, and wherein generating the image comprises generating a color flow image.

13. The method of claim 1 wherein clutter filtering comprises thresholding estimates of flow and wherein generating the image comprises generating a color flow image.

14. In a non-transitory computer readable storage medium having stored therein data representing instructions executable by a programmed processor for motion artifact suppression in medical diagnostic ultrasound, the storage medium comprising instructions for:

detecting at least lateral motion between clutter data acquired at different times, the clutter data estimated to represent a strength of clutter;

determining a threshold value for velocity selected using an amount of the detected at least lateral motion, the threshold value set with a function mapping greater motion to greater threshold values;

estimating velocities; and thresholding the velocities with the threshold value for velocity.

15. The non-transitory computer readable storage medium of claim 14 wherein detecting the at least lateral motion comprises spatially correlating the data from the different times.

16. The non-transitory computer readable storage medium of claim 14 wherein estimating the velocities comprises estimating the velocities for a plurality of locations, and wherein thresholding comprises thresholding for the plurality of locations.

17. The non-transitory computer readable storage medium of claim 14 wherein thresholding comprises setting the velocities below the threshold value to a lower value and maintaining the values of the velocities above the threshold value.

18. In a non-transitory computer readable storage medium having stored therein data representing instructions executable by a programmed processor for motion artifact suppression in medical diagnostic ultrasound, the storage medium comprising instructions for:

detecting at least lateral motion between clutter data acquired at different times, the clutter data estimated to represent a strength of clutter;

determining a threshold value for velocity selected using an amount of the detected at least lateral motion;

setting a clutter filter cutoff frequency and a spectrum shift for data applied to the clutter filter as a function of the detected at least lateral motion estimating velocities; and thresholding the velocities with the threshold value for velocity.

19. A system for motion artifact suppression in medical diagnostic ultrasound, the system comprising:

a beamformer operable to acquire data;

a mixer operable to shift a frequency of the data;

a wall filter operable to high pass filter an output of the mixer;

an estimator operable to estimate flow from an output of the wall filter;

a thresholder operable to threshold the estimated flow; and a processor configured to estimate a degree of motion from two- or three-dimensional spatial correlation and to adapt a setting of the mixer, the wall filter, the thresholder, or combinations thereof, the setting mapped with greater change for a greater degree of motion as a variable mapped to a value of the setting.

20. The system of claim 19 wherein the processor is configured to adapt a velocity threshold of the thresholder based on the degree of motion.

* * * * *